United States Patent [19]

Maestro et al.

[11] Patent Number: 5,395,953
[45] Date of Patent: Mar. 7, 1995

[54] METHOD OF PREPARING HYDRINDANE COMPOUNDS AND HYDRINDANE-RELATED COMPOUNDS

[75] Inventors: Miguel A. Maestro; Antonio Mourino, both of Santiago de Compostela, both of Spain; Benjamin Borsje; Sebastianus J. Halkes, both of Weesp, Netherlands

[73] Assignee: Duphar International Research B.V., Weesp, Netherlands

[21] Appl. No.: 109,708

[22] Filed: Aug. 20, 1993

[30] Foreign Application Priority Data

Aug. 24, 1992 [EP] European Pat. Off. ............ 92202565

[51] Int. Cl.$^6$ .............................................. A01M 43/04
[52] U.S. Cl. ...................................... 552/546; 568/315
[58] Field of Search ........................... 568/315; 552/546

[56] References Cited

PUBLICATIONS

Bovicelli et al, J. Org. Chem., vol. 57, pp. 2182–2184 (1992).
Bovicelli et al, J. Org. Chem., vol. 57, pp. 5052–5054 (1992).
Adam et al, J. Org. Chem., vol. 57, pp. 953–955 (1992).
Mello et al, Tit. Letters, vol. 31, pp. 3067–3070 (1990).
Journal of Organic Chemistry, vol. 44, 1979, pp. 2318–2320, Cohen et al., "Dry Ozonation of Steroids, C–25 Functionalization of Cholestane Derivatives".
Journal of Organic Chemistry, vol. 53, Aug. 5, 1988, pp. 3891–3893, Mello et al., "On the Isolation and Characterization of Methyl9trifluoromethyl)dioxirane".
Tetrahedron Letters, vol. 32, No. 43, Oct. 21, 1991, pp. 6057–6060, Kiegiel et al., "Chemical Conversion of Vitamin D$_3$ To Its 1,25-Dihydroxy Metabolite".
Journal of the American Chemical Society, vol. 113, No. 6, Mar. 13, 1991, pp. 2205–2208, Mello et al., "Oxidations by Methyl(trifluoromethyl)dioxirane. Conversion of Alcohols into Carbonyl Compounds".
Chemical Abstracts, vol. 116, 1992, Columbus, Ohio, US; Abstract No. 58436b *Abstract* & J. Org. Chem. vol. 57, No. 3, 1992, pp. 953–955 W. Adam et al.
Chemical Abstracts, vol. 113, 1990, Columbus, Ohio, US; Abstract No. 230792r, *Abstract* & Chemtracts: Org. Chem. vol. 3, No. 2, 1990, pp. 159–161 Y. D. Wu et al.
Journal of the American Chemical Society. vol. 111, No. 17, 1989, Gaston, Pa., US, pp. 6749–6757 R. Mello et al.
Curci in Proceedings Reunion Hispano–Italiano de Chimica Organico, Valencia, 20–24 Apr. 1992, Abstract 0–21.

*Primary Examiner*—James H. Reamer
*Attorney, Agent, or Firm*—Stevens, Davis, Miller & Mosher

[57] ABSTRACT

The invention relates to a method of preparing a compound having an alkyl or alkoxyalkyl side-chain with a terminal 2-hydroxyprop-2-yl group, by oxidizing a compound having a terminal isopropyl group in its side-chain with a dioxirane as the oxidant.

3 Claims, No Drawings

METHOD OF PREPARING HYDRINDANE COMPOUNDS AND HYDRINDANE-RELATED COMPOUNDS

The invention relates to a method of preparing hydrindane compounds and hydridane-related compounds. Certain hydrindane compounds are useful synthetic tools or synthons in the preparation of vitamin D compounds. Various vitamin D compounds have a strong biological activity and may be used in all those cases in which problems with the calcium metabolism play a part. A few years ago it was found that various active vitamin-D compounds also have other pharmacotherapeutic activities and may be used successfully, for example, for the treatment of certain skin and bone diseases, for cosmetic applications and for treating diseases which are related to cell differentiation, cell proliferation or imbalance in the immune system, including diabetes mellitus, hypertension and inflammatory diseases such as rheumatoid arthritis and asthma. In addition, these compounds may be used in various veterinary applications.

Variations in the $C_{17}$-side chain of the vitamin D molecule may contribute to the diversity in biological activity, in order to attune the structure of the vitamin D compound to the desired activity. A considerable number of biologically interesting vitamin D compounds is provided with a terminal 2-hydroxyprop-2-yl group in the $C_{17}$-side chain. Examples of such active vitamin D compounds are: $1\alpha,25$-dihydroxyvitamin-$D_3$, 25-hydroxyvitamin-$D_3$, 25-hydroxylated 22-oxa-substituted vitamin-D compounds optionally having elongated $C_{17}$-side chains, and 25-hydroxylated vitamin-D compounds having elongated $C_{17}$-side chains, such as 26-homo compounds, 26,27-dihomo compounds, 24,24-dihomo compounds and 24,24,24-trihomo compounds, as well as related vitamin-D compounds having a $C_3$–$C_6$ cycloalkyl group, e.g. a $C_{24}$-cyclopropyl group, in the $C_{17}$-side chain. Furthermore, fluorinated vitamin-D compounds are of importance due to their biological activities.

From the above it will be clear, that the selective oxidation of a terminal isopropyl group of the $C_{17}$-side chain of a suitable synthon to the corresponding 2-hydroxyprop-2-yl group is of great importance, because such starting compounds with a terminal isopropyl group in the $C_{17}$-side chain are in general readily available or accessible.

The oxidation of said terminal isopropyl group in the $C_{17}$-side chain is known in literature. Cohen et al. (J. Org. Chem. 1979, 44, 2318–2320) have oxidized said terminal isopropyl group in certain steroid molecules. The desired 2-hydroxyprop-2-yl compounds were obtained in yields of less than 20%. Kiegiel and coworkers have recently published (Tetrahedron Letters 1991, 32, 6057–6060) results of the oxidation of a suitable synthon for vitamin D compounds, having a $C_{17}$-side chain with a terminal isopropyl group, by using ruthenium tetroxide as the oxidant. The desired tert.C-hydroxylated product was obtained in a 49% overall yield under optimized reaction conditions. It will be clear from the above, that the yields obtained according to the above-described known methods are unsatisfactory.

It is therefore the objective of the present invention to provide a method of preparing a synthon for vitamin D compounds, having a terminal 2-hydroxyprop-2-yl group in the $C_{17}$-side chain, by the selective oxidation of the corresponding terminal isopropyl group, in order to obtain the desired product in an improved yield.

This objective can be achieved by a method of preparing a compound of the general formula

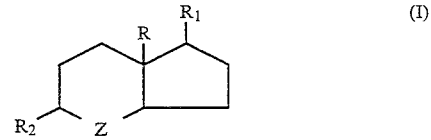

wherein:
R is a methyl group, an ethyl group, a fluorinated ethyl group, a protected hydroxymethyl group or a formyl group;
$R_1$ is an alkyl group or alkoxyalkyl group having 3 to 16 carbon atoms, which group is optionally substituted with one or more substituents selected from cyclopropyl and fluorine, and which group has a terminal 2-hydroxyprop-2-yl group;
Z is a carbonyl group or a protected hydroxymethylene group; and
$R_2$ is a hydrogen atom;
or wherein:
Z and $R_2$, together with the C-atom to which they are commonly attached, constitute a ring system, comprising one ring or more annelated rings, each ring individually having 3-7 ring atoms of which 1-3 atoms may be heteroatoms selected from N, O and S, and optionally being substituted with a substituent selected from the group consisting of a $C_1$–$C_3$ alkyl group, a protected hydroxy group, a halogen atom, an optionally substituted $C_3$–$C_7$ cycloaliphatic group and an optionally substituted phenyl group;
which method is characterized, according to the present invention, in that a compound of the general formula

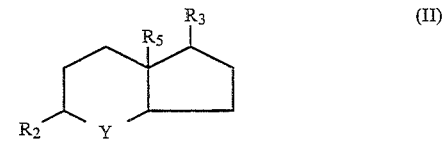

wherein
$R_5$ is a methyl group, an ethyl group, a fluorinated ethyl group, a hydroxymethyl group or a protected hydroxymethyl group;
$R_3$ is an alkyl group or alkoxyalkyl group having 3 to 16 carbon atoms, which group is optionally substituted with one or more substituents selected from cyclopropyl and fluorine, and which group has a terminal isopropyl group;
Y is a hydroxymethylene group or a protected hydroxymethylene group; and
$R_2$ is a hydrogen atom;
or wherein:
Y and $R_2$, together with the C-atom to which they are commonly attached, constitute a ring system, comprising one ring or more annelated rings, each ring individually having 3-7 ring atoms of which 1-3 atoms may be heteroatoms selected from N, O and S, and optionally being substituted with a substituent selected from the group consisting of a $C_1$–$C_3$ alkyl group, a protected hydroxy group, a halogen atom, an optionally substituted $C_3$–$C_7$ cycloaliphatic group and an optionally substituted phenyl group;

is oxidized in one oxidation step by using a dioxirane as the oxidant.

Examples of suitable substituents for the cycloaliphatic substituent or for the phenyl substituent are: $C_1$–$C_3$ alkyl, protected hydroxy, halogen, $C_3$–$C_7$ cycloalkyl and phenyl.

A hydroxy group may be protected by a reaction with a suitable esterification or etherification agent. A suitable esterification agent is an alkylchlorocarbonate having 2 to 5 carbon atoms, or an aromatic carboxylic acid, a saturated aliphatic carboxylic acid having 1 to 4 carbon atoms, p-toluenesulphonic acid, methanesulphonic acid, trifluoroacetic acid or a derivative of these acids suitable for the esterification reaction. In order to protect hydroxy groups in the form of an ether, in principle any etherification agent known for this purpose is suitable: for example, a triphenylmethylhalide, 2,3-dihydropyrane, a trialkylsilylhalide, a diphenylalkylsilylhalide, an alkoxyalkylhalide, a trialkylsilylethoxymethylhalide, or a derivative thereof, the alkyl groups of which have 1 to 6 carbon atoms. Particularly suitable for this purpose are trimethylsilylchloride, tert.-butyldimethylsilylchloride, dimethyl-(1,1,2-trimethylpropyl)silylchloride, trimethylsilyl-ethoxymethylchloride, methoxymethylchloride, methoxyethylchloride, tert.-butyldimethylsilyl trifluoroacetate, or trimethylsilylimidazole, because these etherification agents readily react with the hydroxy group to be protected to form an ether function, which on the one hand is sufficiently stable under the conditions of the reaction or reactions in view, but on the other hand can easily be removed [deprotection], if desired, to recover the original hydroxy group; tert.-butyldimethylsilylchloride is to be preferred, because the tert.-butyldimethylsilyl group has been found to be excellently suitable as a protective group.

Preferably said dioxirane, to be used as an oxidant in the above oxidation reaction, is selected from dimethyl dioxirane, methyl (trifluoromethyl) dioxirane and bis(trifluoromethyl) dioxirane. As will be clear from the Examples, methyl (trifluoromethyl) dioxirane is preeminently suitable, because by using this oxidant the intended selective oxidation can be performed in a substantially quantitative yield.

Oxidations by dioxiranes are known in literature. The isolation of the above-mentioned dioxiranes is described by Mello and coworkers in J. Org. Chem. 1988, 53, 3890–3891. The same authors have disclosed the oxidation of various saturated hydrocarbons by methyl (trifluoromethyl) dioxirane, e.g. of cyclohexane, methyl-substituted cyclohexanes, 2,3-dimethylbutane and adamantane: J. Am. Chem. Soc. 1989, 111, 6749–6757. The selectivity, however, is often not completely satisfactory. For example, the oxidation of methyl-substituted cyclohexanes generally yields a mixture of hydroxylated compounds with substituted cyclohexanones. The conversion of alcohols into carbonyl compounds by methyl (trifluoromethyl) dioxirane is described in a separate publication by Mello et al.: J. Am. Chem. Soc. 1991, 113, 2205–2208. Recently the oxidation of asteroid compound by a dioxirane has been described, viz. by Curci in Proceedings Reunion Hispano-Italiana de Chimica Organico, Valencia, 20–24 Apr., 1992, Abstract O-21. According to this publication, estrone acetate could be oxidized by dimethyl dioxirane in a good yield to the corresponding 9-hydroxy-steroid compound.

In view of the above it is quite a surprise, that the intended oxidation reaction according to the present invention proceeds so selectively. In fact, as will be clear from the Examples, undesired oxidation of the tert.C bonded hydrogen in the ring system, viz. at $C_{14}$ and at $C_{17}$, could not be observed.

The invention more in particular relates to a method of preparing a compound of the general formula

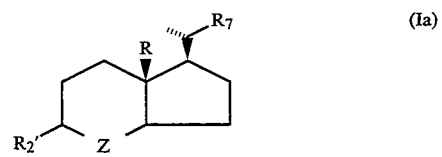

(Ia)

wherein
R has the above meaning;
Z is a carbonyl group or a protected hydroxymethylene group;
$R_7$ is an alkyl or alkoxy group having 3 to 14 carbon atoms, which group is optionally substituted with a cyclopropyl group or with one or two fluorine atoms, and which group has a terminal 2-hydroxy-prop-2-yl group; and
$R_2'$ is a hydrogen atom;
or wherein:
Z and $R_2'$, together with the C-atom to which they are commonly attached, constitute a saturated ring system, comprising one or two annelated $C_3$–$C_7$ cycloalkyl ring(s) and optionally substituted with one or more substituents, which are selected from methyl, protected hydroxy and halogen;
by oxidizing a compound of the general formula

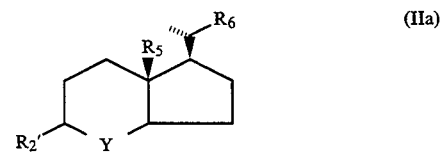

(IIa)

wherein
$R_5$ has the above meaning;
Y is a hydroxymethylene group or a protected hydroxymethylene group;
$R_6$ is an alkyl or alkoxy group having 3 to 14 carbon atoms, which group is optionally substituted with a cyclopropyl group or with one or two fluorine atoms, and which group has a terminal isopropyl group; and
$R_2'$ is a hydrogen atom;
or wherein:
Y and $R_2'$, together with the C-atom to which they are commonly attached, constitute a saturated ring system, comprising one or two annelated $C_3$–$C_7$ cycloalkyl ring(s) and optionally substituted with one or more substituents, which are selected from methyl, protected hydroxy and halogen;
by an dioxirane as defined above.

It is a striking phenomenon, that the selective oxidation according to the invention is restricted to oxidation of the terminal isopropyl group only and does not attack the other tert.C in the $C_1$-side chain of the above compound Ia.

Suitable examples of substituent R are methyl, ethyl, hydroxymethyl and 2,2-difluoroethyl, the introduction of the last three substituents being described in the published European patent application no. 92201851.0 under No. 0521550 on Jan. 1, 1993 in the name of applicants. Suitable examples of substituent $R_6$, which can be used in starting compounds for the above-mentioned terminally hydroxylated vitamin D compounds, are: 4-methylpentyl, 4-methylpentoxy, 4-methylhexyl, 4-methylhexyloxy, 4-ethylhexyl, 4-ethylhexyloxy, 6-methylheptyl, 6-methylheptyloxy, 7-methyloctyl, 7-methyloctyloxy and 3-cyclopropyl-propyl, as well as the corresponding fluor-substituted analogues.

As disclosed by Mello et al. (see above), a hydroxy substituent, e.g. a 4-hydroxy substituent, in the hydrindane molecule, can concurrently be oxidized to the corresponding oxo function.

The invention will now be described in greater detail with reference to the following specific Examples.

EXAMPLE I

Preparation 1-(6-hydroxy-6-methylhept-2-yl)-7a-methylhydrindan-4-one (a) Oxidation by methyl (trifluoromethyl) dioxirane
Reaction equation

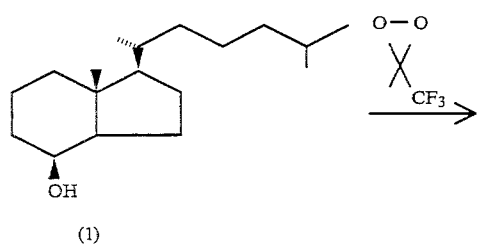

Method of preparation

The starting compound, viz. 1-(6-methylhept-2-yl)-7a-methylhydrindan-4-ol (1), is dissolved in a quantity of 0.34 mmol into 2 ml of dichloromethane and cooled down to −15° C. To this solution, 1.1 ml of a 0.68M solution of methyl (trifluoromethyl) dioxirane (0.75 mmol) in 1,1,1-trifluoropropanone is added at once, and the reaction mixture is stirred at −15° C. for 6 hours. The solvents are removed under reduced pressure and the residue is flash chromatographed (2–8 % EtOAc in hexane) to give the desired product (2) in a yield of 95%.

$^1$H-NMR (CDCl$_3$, 200 MHz): δ 1.48 (6H,s,CH$_3$-26,27), 0.92 (3H,d,CH$_3$-21), 0.57 (3H,s,CH$_3$-18); $^{13}$C-NMR (CDCl$_3$, 50 MHz): δ 212.7, 71.7, 12.3.

(b) Oxidation by dimethyl dioxirane
Reaction equation

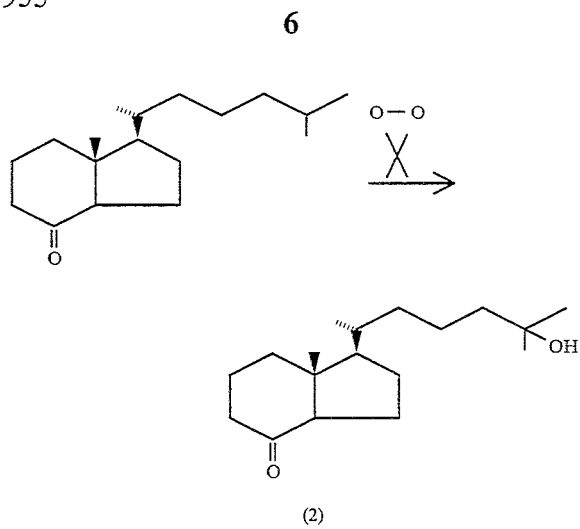

Method of preparation

The starting compound, viz. 1-(6-methylhept-2-yl)-7a-methylhydrindan-4-one (1 equivalent), is dissolved into dichloromethane. To this solution a solution of 3 equivalents of dimethyl dioxirane in acetone is added at room temperature. The reaction mixture is stirred at 20° C. for 48 hours, producing the title compound in a yield of 86%. The product obtained, after the work-up procedure as described under (a), is identical with the product prepared under (a).

EXAMPLE II

Preparation of 25-hydroxy-5,6-dibromocholestanol acetate

Reaction equation

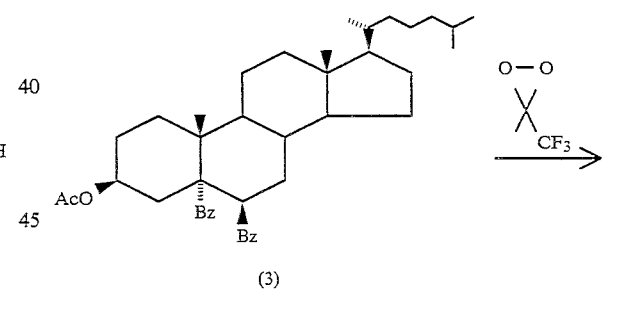

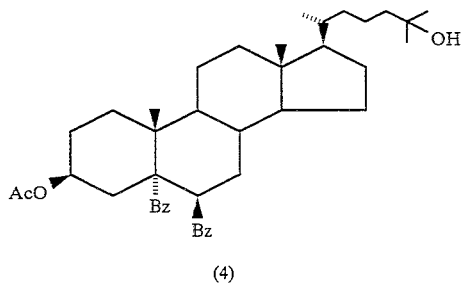

In a corresponding manner as described in Example I(a), the title compound (4) is prepared from 5,6-dibromocholestanol acetate (3) in a yield of 72%. The product is identified by its NMR spectra:

$^1$H-NMR (CDCl$_3$, 20 MHz): δ 5.48 (1H,m,H-3), 4.82 (1H,m,H-6), 2.05 (3H,s,OAc), 1.46 (3H,s,CH$_3$-19), 1.22 (6H,s,CH$_3$-26,27), 0.93 (3H,d,CH$_3$-21), 0.71 (3H,s,CH$_3$-13);

13C-NMR (CDCl3, 50 MHz): δ170.4, 80.1, 72.0, 71.1, 56.1, 56.0, 55.1, 47.2, 44.3, 42.7, 41.8, 39.5, 37.2, 36.5, 36.4, 35.7, 30.8, 29.7, 29.3, 29.2, 28.2, 26.2, 24.0, 21.3, 21.2, 20.3, 20.1, 18.6, 12.2.

We claim:

1. A method of preparing a compound of the general formula

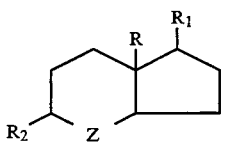

(I)

wherein
R is a methyl group, an ethyl group, a fluorinated ethyl group, a protected hydroxymethyl group or a formyl group;
$R_1$ is an alkyl group or alkoxyalkyl group having 3 to 16 carbon atoms, which group is optionally substituted with one or more substituents selected from cyclopropyl and fluorine, and which group has a terminal 2-hydroxyprop-2-yl group;
Z is a carbonyl group or a protected hydroxymethylene group; and
$R_2$ is a hydrogen atom;
or wherein:
Z and $R_2$, together with the C-atom to which they are commonly attached, constitute a ring system, comprising one ring or more annelated rings, each ring individually having 3–7 ring atoms of which 1–3 atoms may be heteroatoms selected from N, O and S, and optionally being substituted with a substituent selected from the group consisting of a $C_1$–$C_3$ alkyl group, a protected hydroxy group, a halogen atom, an optionally substituted $C_3$–$C_7$ cycloaliphatic group and optionally substituted phenyl group;
said method being characterized in that a compound of the general formula

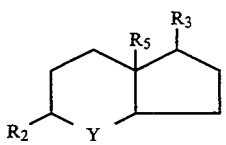

(II)

wherein
$R_5$ is a methyl group, an ethyl group, a fluorinated ethyl group, a hyroxymethyl group or a protected hydroxymethyl group;
$R_3$ is an alkyl group or alkoxyalkyl group having 3 to 16 carbon atoms, which group is optionally substituted with one or more substituents selected from cyclopropyl and fluorine, and which group has a terminal isopropyl group;
Y is a hydroxymethylene group or a protected hydroxymethylene group; and
$R_2$ is a hydrogen atom;
or wherein:
Y and $R_2$ together with the C-atom to which they are commonly attached, constitute a ring system, comprising one ring or more annelated rings, each ring individually having 3–7 ring atoms of which 1–3 atoms may be heteroatoms selected from N, O and S, and optionally being substituted with a substituent selected from the group consisting of a $C_1$–$C_3$ alkyl group, a protected hydroxy group, a halogen atom, an optionally substituted $C_3$–$C_7$ cycloaliphatic group and an optionally substituted phenyl group; is oxidized in one oxidation step by using a dioxirane selected from the group consisting of dimethyl dioxirane, methyl (trifluoromethyl) dioxirane and bis(trifluoromethyl) dioxirane as the oxidant.

2. A method as claimed in claim 1, characterized in that the starting compound of formula II is oxidized by using methyl (trifluoromethyl) dioxirane as the oxidant.

3. A method as claimed in claim 1 of preparing a compound of the general formula

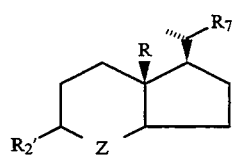

(Ia)

wherein
R has the meaning given in claim 1;
Z is a carbonyl group or a protected hydroxymethylene group; and
$R_7$ is an alkyl or alkoxy group having 3 to 14 carbon atoms, which group is optionally substituted with a cyclopropyl group or with one or two fluorine atoms, and which group has a terminal 2-hydroxyprop-2-yl group; and
$R_2'$ is a hydrogen atom;
or wherein
Z and $R_2'$, together with the C-atom to which they are commonly attached, constitute a saturated ring system, comprising one or two annelated $C_3$–$C_7$ cycloalkyl ring(s) and optionally substituted with one or more substituents, which are selected from methyl, protected hydroxy and halogen;
said method being characterized in that a compound of the general formula

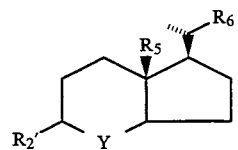

(IIa)

wherein
$R_5$ has the meaning given in claim 1;
Y is a hydroxymethylene group or a protected hydroxymethylene group;
$R_6$ is an alkyl or alkoxy group having 3 to 14 carbon atoms, which group is optionally substituted with a cyclopropyl group or with one or two fluorine atoms, and which group has a terminal isopropyl group; and
$R_2'$ is a hydrogen atom;
or wherein
Y and $R_2'$, together with the C-atom to which they are commonly attached, constitute a saturated ring system, comprising one or two annelated $C_3$–$C_7$ cycloalkyl ring(s) and optionally substituted with one or more substituents, which are selected from methyl, protected hydroxy and halogen; is oxidated by using a dioxirane selected from dimethyl dioxirane, methyl (trifluoromethyl) dioxirane and bis(trifluoromethyl) dioxirane as the oxidant.

* * * * *